# (12) United States Patent
Daniel et al.

(10) Patent No.: US 7,547,510 B2
(45) Date of Patent: Jun. 16, 2009

(54) THERMOSTABLE PROTEINASES FROM THERMOPHILIC BACTERIA

(75) Inventors: Roy McIver Daniel, Hamilton (NZ); David James Saul, Auckland (NZ)

(73) Assignee: Zygem Corporation Limited, Hamilton (NZ)

( * ) Notice: Subject to any disclaimer, the term of this patent is extended or adjusted under 35 U.S.C. 154(b) by 176 days.

(21) Appl. No.: 10/477,422

(22) PCT Filed: May 14, 2002

(86) PCT No.: PCT/NZ02/00093

§ 371 (c)(1), (2), (4) Date: Jun. 1, 2004

(87) PCT Pub. No.: WO02/092844

PCT Pub. Date: Nov. 21, 2002

(65) Prior Publication Data

US 2004/0197788 A1    Oct. 7, 2004

(30) Foreign Application Priority Data

May 14, 2001    (NZ)    ..................... 511680

(51) Int. Cl.
  *C12Q 1/68*    (2006.01)
  *C12P 19/34*    (2006.01)
  *C07H 21/00*    (2006.01)
(52) U.S. Cl. .......................... 435/6; 435/91.2; 536/25.4
(58) Field of Classification Search .................. None
  See application file for complete search history.

(56) References Cited

U.S. PATENT DOCUMENTS

| | | | |
|---|---|---|---|
| 4,442,214 A * | 4/1984 | Morgan et al. ........... | 435/252.1 |
| 6,261,822 B1 | 7/2001 | Takakura et al. | |
| 6,469,159 B1 | 10/2002 | Belly et al. | |
| 6,762,027 B2 | 7/2004 | Greenfield et al. | |
| 7,001,724 B1 * | 2/2006 | Greenfield ..................... | 435/6 |

FOREIGN PATENT DOCUMENTS

| | | | |
|---|---|---|---|
| EP | 0071515 B1 | | 10/1985 |
| NZ | 233270 A | * | 2/1993 |
| WO | WO 9851693 A1 | * | 11/1998 |
| WO | WO-02/092844 A1 | | 11/2002 |
| WO | WO-03/064605 A2 | | 8/2003 |

OTHER PUBLICATIONS

Toogood et al. Purification and characterization of AK. 1 protease, a thermostable subtillsin with a disulfide bond in the substrate-binding cleft. Biochemical Journal (2000) 350: 321-328.*
Kwon et al. Extracellular alkaline proteases from alkalophilic Vibrio metschnikovii Strain RH530. Biotechnology Letters. (1994) 16(4): 413-418.*

Jung et al. Analysis of DNA from a Beta procumbens chromosome fragment in sugar beet carrying a gene for nematode resistance. Theoretical and Applied Genetics (1990) 79:663-672.*
Toogood, H. S. Perification and Characterization of AK.1 Proteaaw, A Theremo Stable Subtilisin with A Disulfide Bond in the Substrate Binding Cleft. Biochemical Journal, 2000 350 (PT 1): 321-8.
Saul, D, J. et al. Sequence of the Gene Encoding A Highly Thermostable Neutral Proteinase From *Bacillis* sp Strain EA 1: Expression in *Escherichia coli* and Characterization. Biomedia et Biophysica Acta 1996 1308(1) 74-80.
Nishiya In; Imkanaka, T. Cloning and Nucleotide Sequences of the *Bacillis starothermophilus* Neutral Proteinase Gene and its Transcriptional Activator Gene Journal of Bacteriology 1990 172(9) 4861-9.
Borges, K. M. et al A Rapid Method for Preparation of Bacterial Chromosomal DNA in Agarose Plugs Using Thermus RT 41 A Proteinase. Biotechniques 1992 12(2): 222-223.
Bryan PN et al, Proteinases of Enhanced Stability: Characterization of A Thermostable Variant of Substilisin 1986 1(4) 326-34.
Vanden Berg B. et al. A Highly Thermostable Neutral Protease Form *Bacillis caldolyticus*: Cloning and Expression of the Gene in *Bacillis subtilis* and Characterization of the Gene Product Journal of Bactriology 1991 173(13) 4190-15.
Pavlova IN, Zholner LG. The Serine Proteases of Thermohilic *Bacilli mikrobiologia* 1988 56(5) 8-16 Abstract (Article in Russion.
Pretaq™ Thermostable Proteinase Roche Biochemica No. 2 New Products 1995 P5.
Proteinase K Fermentas Catalog 2000-2001.
"More New Products to Meet your Changing Needs," (1995). *Biochemica*, No. 2, pp. 4-7.
Haseltine, C. et al. (Jan. 2001). "Secreted Euryarchaeal Microhalocins Kill Hyperthermophilic Crenarchaea," *Journal of Bacteriology* 183(1):287-291.
International Search Report mailed Jul. 12, 2002, for PCT Application No. PCT/NZ02/00093 filed May 14, 2002, 4 pages.
Montoya, D. et al. (2001). "New Solvent-Producing Clostridium sp. Strains, Hydrolyzing a Wide Range of Polysaccharides, are Closely Related to Clostridium butyricum," *Journal of Industrial Microbiology & Biotechnology* 27:329-335.
Pavlova, I. N. et al. (May-Jun. 1988). "Serine Proteinase with Lytic Properties," *Mikrobiologilia* 57(3):398-404. (English abstract attached).
Spann, T. P. et al. (May 1996). "Mutagenesis and Gene Identification in Dictyostelium by Shotgun Antisense," *Proceedings of the National Academy of Sciences of the United States of America* 93:5003-5007.
Supplementary European Search Report mailed Aug. 31, 2004, for EP Application No. 02738990.7 filed May 14, 2002, 3 pages.
"Autocatalysis," from Wikipedia, The Free Encyclopedia, located at <http://en.wikipedia.org/wiki/Autocatalysis> visited on May 7, 2007. (1 page).
Coolbear, T. et al. (1991). "Screening of Strains Identified as Extremely Thermophilic *Bacilli* for Extracellular Proteolytic Activity and General Properties of the Proteinases from Two of the Strains," *Journal of Applied Bacteriology* 71:252-264.

(Continued)

*Primary Examiner*—Kenneth R. Horlick
*Assistant Examiner*—Angela Bertagna
(74) *Attorney, Agent, or Firm*—Morrison & Foerster LLP

(57) ABSTRACT

The present invention relates to thermostable proteinases from thermophilic Bacillus species and their uses in the preparation of nucleic acid samples. The enzymes of the invention are stable and active at 65-80° C., but are readily autolysed or denatured above 90° C.

7 Claims, 1 Drawing Sheet

OTHER PUBLICATIONS

Daniel, R. M. et al. (1982). "A Correlation Between Protein Thermostability and Resistance to Proteolysis," *Biochemical Journal* 207:641-644.

Goncalves, V. M. M. et al. (2003). "Purification of Capsular Polysaccharide from *Streptococcus pneumoniae* Serotype 23F by a Procedure Suitable for Scale-Up," *Biotechnology and Applied Biochemistry* 37:283-287.

International Preliminary Examination Report completed Sep. 5, 2003, for PCT Application No. PCT/NZ02/00093 filed May 14, 2002, 5 pages.

International Search Report mailed Sep. 29, 2005, for PCT Application No. PCT/NZ2005/000133 filed Jun. 17, 2005, 3 pages.

International Written Opinion mailed Sep. 29, 2005, for PCT Application No. PCT/NZ2005/000133 filed Jun. 17, 2005, 5 pages.

McMullin, B. (1999). "Some Remarks on Autocatalysis and Autopoiesis," presented at the workshop "Closure: Emergent Organizations and their Dynamics," May 3-5, 1999, University of Ghent, Belgium, located at <http://elm.eeng.dcu.ie/~alife/bmcm9901/html-multi/>visited on May 7, 2007. (2 pages).

Moss, D. et al. (2003). "An Easily Automated, Closed-Tube Forensic DNA Extraction Procedure Using a Thermostable Proteinase," *International Journal of Legal Medicine* 117:340-349.

Pavlova, I. N. et al. (1994). "The Serine Proteinases of Thermophilic *Bacilli*," *Mikrobiolohichnyi Zhurnal* 56:8-16. (English abstract attached and on p. 15).

Promega Corporation. (Aug. 2006). "Product Contents/Quality Control Assays for Proteinase K: Part No. V302B, Size 100mg," Part# 9PIV302, 1 page.

Promega Corporation. (Aug. 2006). "Usage Information," Part# 9PIV302, 1 page.

Supplementary European Search Report mailed May 2, 2008, for EP Application No. 05757530.0 filed Jun. 17, 2005, 3 pages.

Munro, GKL, et al. A Gene Encoding A Thermophilic Alkaline Serine Proteinase from *Thermus* sp. Strain RT41A and its Expression in *Escherichia coli*. Microbiology, Society for General Microbiology, Reading GB vol. 141, No 7, pp. 1731-1738, XP000618229 ISSN 1350-0872, figure 3 published 1995.

Saul, D.J. et al., "Sequence of the Gene Encoding A Highly Thermostable Neutral Proteinase from *Bacillus* sp. Strain EA 1: Expression in *Escherichia coli* and Characterization"; Biochimica et Biophysica Acta; Amsterdam, NL vol. 1308 (Jul. 31, 1998) pp. 74-80; XP001191007 ISSN 0006-3002.

TooGood, HS et al., Purification and Characterization of AK.1 Protease, A Thermotable Subtilisin with a Disulfide Bond in the Substrate-Binding Cleft; Biochemical Journal, The Biochemical Society, London, GB, vol. 350, Part 1, 2000, pp. 321-328; XP001191006 ISSN 0264-6021.

Fung, MC et al.:PCR Amplification of Messenger RNA Directly From A Crude Cell Lysate Prepared By Thermophilic Protease Digestion; Nucleic Acids Research, vol. 19, No. 15 p. 4300; 1991; XP002292318 ISSN 0305-1048.

Moul, Judd W et ak., Absent Ras Gene Mutations in Human Adrenal Cortical Neoplasms and Pheochromocytomas; Journal of Urology; vol. 149, No. 6 pp. 1389-1394; 1993; XP008033915; ISSN 0022-5347.

Peek Keith et al. Some Characteristics of Proteinase From A Thermophilic *Bacillus* sp. Expressed in *Escherichia coli:* Comparison of the Native Enzyme and its Processing in *Escherichia coli* and In Vitro; Applied and Environmental Microbiology, vol. 59, No. 4 pp. 1168-1175 1993 XP00292319 ISSN 0099-2240.

\* cited by examiner

FIGURE 1 is a comparison of the steps involved with DNA extraction using a standard protocol and the new proteinases.
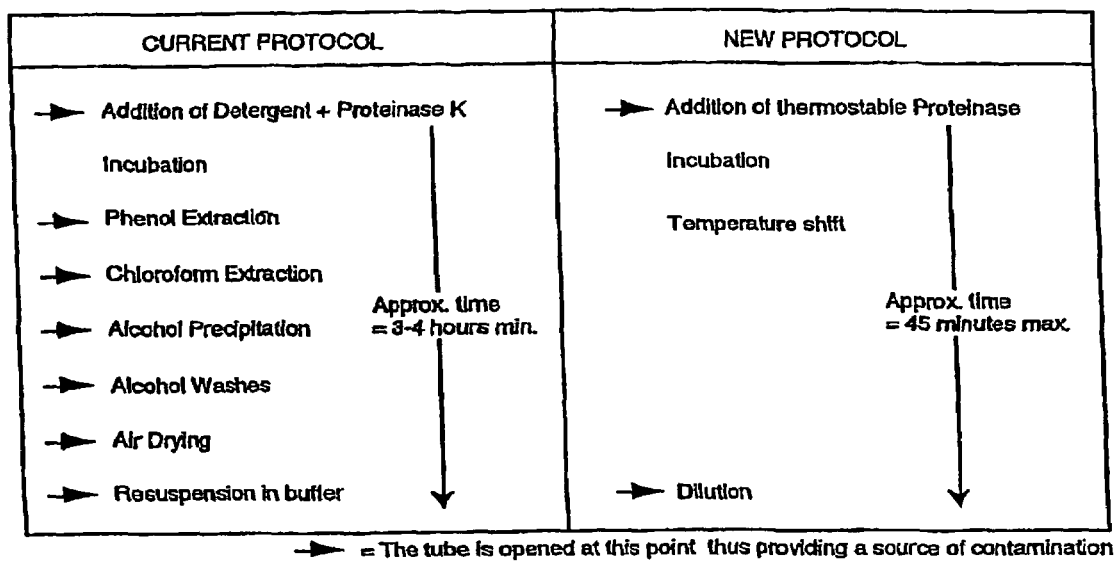
FIGURE 2
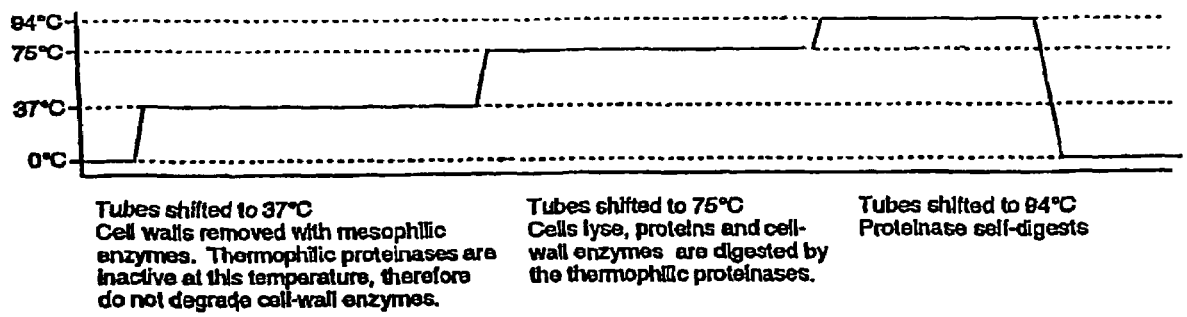

THERMOSTABLE PROTEINASES FROM THERMOPHILIC BACTERIA

TECHNICAL FIELD

This invention relates to improved procedures for molecular biology techniques. In particular, it is envisaged the procedure will facilitate improved molecular biology diagnostic techniques by providing means of removing extraneous contamination, as well as simplifying the overall procedures.

Preferably the contamination that is removed as a consequence of the present invention includes proteins and nucleases.

BACKGROUND ART

Polymerase chain reaction (PCR) has rapidly become one of the most widely used techniques in molecular biology. It is a rapid, inexpensive and simple means of producing relatively large numbers of copies of DNA molecules (via enzymatic amplification of a specific nucleic acid sequence of interest) from minute quantities of source material, even when the source nucleic acid is of relatively poor quality.

A standard PCR involves preparation of the sample, the master mix of reagents and the oligonucleotide primers, followed by detection and analysis of the reaction products.

Although any protocol of template nucleic acid preparation is acceptable for PCR purposes, it is often best to use as few steps as possible in the nucleic acid preparation in order to prevent yield reduction and/or accidental contamination with unwanted nucleic acid.

Nucleic acid-based diagnostic procedures in commercial and academic laboratories often require nucleic acid extractions from natural substances. Applications range from forensic DNA-fingerprinting to medical, agricultural and environmental monitoring. It is important that any nucleic acid extraction be free from contamination particularly where concentration of nucleic acid in the initial sample is very low and/or where contamination can lead to incorrect outcomes.

This is particularly the case in forensic and evidential analyses where quantities of starting material may be measured in picograms or less. Contamination of the sample may occur simply as a result of the sample tube being opened to the atmosphere or being touched by a technician.

Because of the ease with which a sample can be contaminated, it is a requirement that reproducible nucleic acid extraction techniques are free from contamination and require protocols directed to minimising such contamination.

Standard nucleic acid extraction techniques are problematic as the sample tube may require opening and shutting at stages throughout the extraction procedure. It would therefore be advantageous to develop a protocol enabling simple, closed-tube reactions minimising the likelihood of contamination.

PCR technology often necessitates lengthy purification procedures. These procedures involved long incubations with proteinases, phenol and chloroform extractions, and finally an ethanolic salt precipitation.

Numerous methods have been described for the preparation of nucleic acid from animal tissue for amplification by PCR. A typical example is described by Hunt, Parks and Limley (1997) *Food Chemistry* Vol 60: 437-442.

Typically methods for DNA extraction from animal tissue samples (such as meat or bone) contain the following steps:
1) Resuspension of the tissue sample in a buffer containing sodium dodecyl-sulphate (SDS).
2) Homogenisation.
3) Incubation with the enzyme proteinase K for 1-2 hours.
4) Solvent extraction of the sample with phenol.
5) Solvent extraction with a mixture of phenol/chloroform/isoamylalcohol.
6) Solvent extraction with chloroform.
7) Precipitation for a minimum of 1 hour in 3M sodium acetate and 3 volumes of ethanol.
8) Centrifugation of DNA.
9) Washing of the pellet 2 times in ethanol.
10) Air-drying and resuspension of the pellet in buffer.

Simpler methods are available for the release of DNA from blood. Most commonly, the commercial product Chelex™ is used. These methods provide moderate yields of DNA by simply boiling the sample in the presence of this agent.

However, to remove inhibition of the PCR, forensic scientists routinely pre-wash and centrifuge blood cells to lyse the red cells and remove the haem. This necessitates a further step and source of contamination to the procedure and results in a loss of yield with degraded or environmentally compromised blood samples (typical of crime-scene samples).

The applicant has conducted experiments which show nucleic acid extraction using new proteinases removes this inhibition, thus eliminating the need for this step and resulting in a reduced potential for contamination of samples and an improved yield.

Other standard techniques used in molecular biology may also benefit from simple, closed tube reactions, for example the removal of restriction enzymes and phosphatases that are not heat labile and require time consuming phenol/chloroform extractions, ethanolic salt precipitations and wash steps to purify the sample.

All references, including any patents or patent applications cited in this specification are hereby incorporated by references. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only tile listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to one aspect of the present invention there is provided a method for the preparation of nucleic acid samples in a closed system, including the steps of:
 i) adding at least one thermophilic proteinase to a sample containing nucleic acid for testing, and ii) incubating said sample for a preferred period at 65-80° C. as required to effect one or more of lysis of cells, digestion of proteins, digestion of cell-wall enzymes, via activity of said thermophilic proteinase, said method characterised by the step of said thermophilic proteinase having the features of by selected from a group of proteinase being substantially stable and active at 65-80° C. but which is readily autolysed and/or denatured when said sample is incubated at or above 90° C. without requiring the addition of further denaturing agents.

For ease of reference throughout the specification, the term "nucleic acid" will herein be referred to as DNA. However, this should not been seen as a limitation for the method could also be used for the preparation of RNA samples.

While in preferred embodiments of the present invention a thermophilic proteinase is used; it is anticipated thermophilic enzymes other than proteinases could also conceivably be used.

For ease of reference throughout the specification, the thermophilic enzyme will herein be referred to as a proteinase. However, this should not been seen as a limitation for other enzymes could also conceivably be used.

The preferred incubation temperature required to effect one or more of lysis of cells, digestion of proteins, digestion of cell-wall enzymes, via activity of the proteinase is 75° C.

The preferred incubation temperature required to effect autolysis and/or denaturation of the proteinase is 94° C.

However, it should be appreciated these temperatures are given by way of example only and are not meant to be limiting in any way.

It is anticipated that the proteinases will have differing profiles for both enzyme activity and stability over a range of temperatures and that such enzyme dynamics would be known to a skilled addressee. It is also anticipated such enzyme profiles for the proteinases of the present invention could be determined with minimal experimentation.

According to another aspect of the present invention there is provided a method for preparation of nucleic acid samples substantially as described above, said method including the initial steps of:
i) adding at least one mesophilic enzyme and at least one non-specific thermophilic enzyme to a sample containing nucleic acid for testing, and
ii) incubating said sample for a preferred period below 40° C. as required to effect removal of any cell walls via activity of said mesophilic enzyme.

In preferred embodiments the mesophilic enzyme is a cellulase or other cell wall degrading enzyme.

The preferred initial incubation temperature required to effect removal of any cell walls via activity of said mesophilic enzyme is 37° C. Once again, this should not be seen as a limitation in any way.

Proteolytic enzymes derived from both mesophilic and moderately thermophilic organisms are considered of great economic importance, with microbial proteinases taking a large market share of commercial enzymes. The thermal stability of enzymes derived from thermophilic organisms ensures such enzymes have a number of potential applications. A number of thermophilic micro-organisms that produce extracellular proteinases having commercial applications, because of their high intrinsic stability to extreme environments, have been the focus for this invention.

In preferred embodiments however, the proteinase source include *Bacillus* sp. strain EA1 being a neutral proteinase, and *Bacillus* sp. str. Ak1 being a serine proteinase.

The EA1 proteinase is a member of the *Bacillus* 16S rRNA group 5 (which includes *B. stearothermophilus*), isolated from Mount Ercbus, Antarctica EA1's proteinase thermostability lends itself to use in the present procedure.

The *Bacillus* Ak.1 is a thermophilic bacterium that produces an extracellular serine proteinase. Ak.1 proteinase is a thermostable subtilisin. Ak.1 proteinase was purified to homogeneity from the *Escherichia coli* clone PB5517. *Bacillus* strain Ak1 is related to *Bacillus* strain EA1 but more closely resembles *B. thermoglucosdasicus*. This organism was isolated in Auckland as a contaminant of EA1.

The purification, characterisation and genetic sequences of Ak1 and EA1 have previously been published and the reader is referred to the following references:

Toogood H S et al. Purification and characterization of Ak1 protease, a thermostable subtilisin with a disulphide bond in the substrate-binding cleft. Biochemical Journal 2000. 350(Pt 1): 321-8.

Saul D J et al. Sequence of the gene encoding a highly thermostable neutral proteinase from *Bacillus* sp. strain EA1: expression in *Escherichia coli* and characterisation. Biochimica et Biophysica Acta. 1996. 1308(1): 74-80.

The requirement for a proteinase in this invention is that:
1) it is substantially stable and active within the range 65-80° C.,
2) it is able to be readily autolysed and/or denatured at or above 90° C. and optionally
3) it has a temperature-activity profile such that it has low activity below 40° C. (so accompanying mesophilic enzymes, for example cellulase, are not degraded).

The present invention is also directed to a selection method for identifying proteinases with these characteristics.

The Ak1 proteinase was originally investigated to determine its usefulness in the clean-up of DNA at high temperatures. However, a broad substrate specificity was deemed required for efficient protein removal, such as was obtained with the commercially available Rt41A proteinase. As it was found that the Ak1 proteinase had a limited substrate specificity, its application was not explored further (Toogood et al. Biochem. J. (2000) 350, 321-328).

The Rt41A proteinase is a thermostable alkaline proteinase that is known commercially as PreTaq™, being used in the preparation of DNA and mRNA prior to amplification by PreTaq™—*Thermus* sp. str. Rt41A is a $Ca^{2+}$-dependent serine proteinase. The Rt41A is a species that groups within a family of *Thermus* species so far found only in New Zealand.

Standard DNA extraction protocols involve incubating samples with Proteinase K, causing lysis of cells at temperatures where deleterious enzymes released from the cells are active that may degrade sample DNA.

The use of thermophilic proteinases allows DNA extraction and cell lysis to be carried out at temperatures where these deleterious enzymes are inactive, thus preserving the DNA.

PreTaq™ is commercially available as a thermostable alternative to Proteinase K to clean up DNA without degradation.

However, the temperature-activity profile of PreTaq™ is not ideal as it remains active and not readily removed at high temperatures, and thus itself becomes a contaminant. EA1 and Ak1 proteinases have been identified by the applicants as alternative thermostable $Ca^{2+}$-dependent proteinases that are easier to remove at high temperatures.

In the present invention it is envisaged that the $Ca^{2+}$ concentration is optimised.

In preferred embodiments, thermostable proteinases are added to the sample tube. The sample tube is then incubated and subjected to a temperature shift. Following the temperature shift, protein degradation occurs.

The procedure operates at 65-80° C. as these enzymes are highly active between these temperatures. At this temperature, the cells are lysed and the proteinases degrade any contaminating protein. In particular, they rapidly remove DNA-degrading nucleases at temperatures where these nucleases are inactive, thereby minimising DNA degradation of the sample.

The present invention has been directed to the development of an improved protocol using one of two thermophilic proteinases to extract DNA from a range of substances in a simple closed-tube reaction.

The development of a simple, closed tube system has many advantages over the prior art. Current DNA extraction procedures are lengthy, require the use of a number of toxic chemicals such as phenol; and numerous steps which require opening and closing of tubes allow contamination to readily occur.

The closed-tube system of the present invention allows DNA extraction substantially free of contamination and at a high yield, which can be used without lengthy purification steps in a wide range of diagnostic techniques.

The procedure of the present invention relies on the proteinase and/or proteinase/cell-wall degrading enzyme cocktail having differential activities at different temperatures. By cycling through the variable temperatures, the activities of different enzymes can be brought into play without the need for opening tubes to add new reagents.

The new procedures are directed to purifying nucleic acid by requiring the tube only be opened to add the sample initially and then subsequently opening it for testing. Accordingly, the procedure is faster and not prone to the introduction of contaminants as are previously used protocols.

The present method is thus directed to improving the standard of molecular biology diagnostic techniques, such as PCR, and minimising contamination of samples as a result of opening and shutting sample tubes.

For PCR-based applications, the proteinases can be removed subsequently by heating the samples to 90° C. or above, which results in rapid auto-catalysis (self-digestion or denaturation). Reaction buffers are also similar to that most commonly used in the polymerase chain reaction (PCR). These two factors remove the need for phenol/chloroform extraction and ethanolic salt precipitation steps of current protocols, thereby resulting in significant improvements in yield of DNA and a much reduced risk of contamination or exposure to toxic chemicals.

For applications that require low temperature digestion of DNA (for example, restriction enzyme digestion of DNA), the proteinases need not be removed as they have very low activity at 37° C. Accordingly this makes them ideal for other diagnostic techniques such as the preparation of plugs for pulse field gel electrophoresis, where otherwise extensive washing to remove Proteinase K is required.

The proteinases also allow restriction digested DNA to be used for DNA ligation without lengthy purification protocols to remove the restriction enzymes. After incubation at 37° C., the sample tubes may be heated to 65-80° C. to allow the proteinases to remove the restriction enzymes. These temperatures do not denature the DNA. Following this incubation the samples are cooled for the low temperature ligation reactions, which are carried out at room temperature or below.

As the thermophilic proteinases have very low activity at low temperatures, they need not be removed.

Where multistep or multi-enzyme reactions are required, the proteinases can be used in an enzyme mixture. As there is such low activity below 40° C., other enzyme reactions are able to occur in the presence of the proteinases. Mixtures of the mesophilic enzymes active at lower temperatures and one of the above mentioned proteinases can be used to weaken and/or remove cell walls from plant and fungal tissue and bacteria, spores and biofilms before continuing with the closed-tube DNA extraction procedure of the present invention.

This invention also lends itself to the development of a set of protocols and kit formulations for DNA extraction to overcome problems experienced with currently employed DNA extraction strategies, which are time-consuming, inefficient and prone to contamination.

An example of this is the range of Whatman FTA® products. These products are relatively new tools in forensic DNA analysis, containing protein denaturants, chelating agents and a free radical trap designed to protect and entrap the nucleic acid In forensic applications, FTA® cards are most commonly used for the collection of reference samples such as blood. The DNA in the sample binds to the FTA® substrate whilst other material in the sample (inhibitors such as haem) is removed by a series of washing steps.

A primary advantage of FTA® cards is their amenability to automation, as all steps in the process can be carried out in a single tube using robotics. However, although the cards are effective in their intended use, recommended washing steps are time consuming and involve multiple tube openings, increasing the risk of contamination.

By using EA1 protease, the aforementioned protocols require no wash steps and so the enzyme was tested for efficacy with DNA extraction from FTA® card samples.

Extraction using EA1 protease was found to be effective and simpler than recommended procedures. In addition, it appears to normalise the amount of DNA bound to the card and hence provides a more controlled source of template to the subsequent PCR amplification.

As a result of this normalisation, variation between profiles is reduced significantly when compared to profiles using the manufacturer's procedures. The heating steps in the EA1 extraction process appear to remove excess DNA not adhered to the card, leaving only the tightly-bound molecules.

This conclusion is supported by measurements of the yield of DNA produced by the EA1 system. EA1 extraction gives a lower average yield than that obtained using the manufacturer's method, but more significantly, produces yields with a reduced variation. As a result of this effect, more consistent STR profiles are obtained and fewer profiles are rejected due to inconsistent peak height.

Whilst the present invention is directed to the use of the preferred mesophilic and thermophilic enzymes for use in improved PCR techniques in particular, it should be appreciated that the present invention may have applications for a range of DNA diagnostic techniques where clean-up of DNA to remove contaminants is particularly beneficial, or for diagnostic techniques where the present invention may be adapted to achieve a similar beneficial outcome.

Accordingly, this invention is directed to the development of improved proteinases and in research for the use of such enzymes in molecular biology diagnostic techniques.

BRIEF DESCRIPTION OF DRAWINGS

Further aspects of the present invention will become apparent from the following description, given by way of example only and with reference to the accompanying drawings in which:

FIG. 1 is a comparison of the steps involved in DNA extraction using a standard protocol and the new protocol using proteinases in accordance with one preferred embodiment of the present invention; and FIG. 2 is a diagrammatic representation of the activities occurring at different temperatures using the new DNA extraction protocol in accordance with one preferred embodiment of the present invention.

BEST MODES FOR CARRYING OUT THE INVENTION

With reference to the figures by way of example only, there is provided a method for the preparation of DNA samples for polymerase chain reaction which removes contaminating proteins and inhibitors from samples, and provides an alternative to existing procedures.

FIG. 1 illustrates the difference in the number of steps, time taken and likely introduction of contaminants between standard protocols and the improved protocol of the present invention.

The method of the present invention also preferably includes the addition of at least one mesophilic enzyme and at least one non-specific thermophilic enzyme to a sample containing DNA for testing and amplification via PCR.

The sample is then incubated for a preferred period at 37° C. to effect removal of any cell walls via activity of the mesophilic enzymes.

The temperature is then increased to 75° C. as required to effect one or more of lysis of cells, digestion of proteins, digestion of cell-wall enzymes, via activity of the thermophilic enzymes, wherein said enzymes are proteinases.

A further increase in temperature to 94° C. effects selfdigestion and/or denaturation of the thermophilic proteinases.

Cycling the sealed tubes from 37-75-94° C. will first degrade any cell walls or protective layers, next degrades the mesophilic enzymes and finally degrade or denature the thermophilic proteinases.

The procedure relies on the proteinase or proteinase/cell-wall degrading enzyme cocktail having differential activities at different temperatures. By cycling through the variable temperatures, different enzyme activities can be brought into play without the need for opening tubes to add new reagents.

Accordingly, the procedure is quick and not prone to the introduction of contaminants as are previously used protocols.

The preferred method is characterised by the use of thermophilic proteinases which are substantially stable and active at 75° C. but which are readily autolysed and/or denatured when said sample is incubated at 94° C.

Thermophilic proteinases selected for use with the present invention include a proteinase derived from *Bacillus* sp. including *Bacillus* sp. str. EA1, being a neutral proteinase, and *Bacillus* sp. str. Ak1, being a serine proteinase.

In a standard procedure for use with animal tissue, reagents would first be added on ice to ensure minimal DNA degradation. The sample tubes would then be shifted to 75° C. where cells lyse and proteins denature and are digested by the thermophilic proteinases. There is minimal DNA degradation occurring at this stage by endogenous nucleases. Tubes are then shifted to 94° C. where the thermophilic proteinase self-digests and/or denatures.

A modified procedure in accordance with one embodiment of the present invention is presented in FIG. 2 where alternative enzymes are required to degrade cell walls (particularly useful for plant and fungal extractions), as follows:

a) Tubes are shifted to 37° C. and cell walls are removed with mesophilic enzymes. Thermophilic proteinases are inactive at this temperature and therefore do not degrade the cell-wall enzymes.

b) The sample tubes are then transferred to 75° C. where the cells lyse and proteins and cell wall enzymes are digested by the thermophilic proteinases.

c) The tubes are then transferred to 94° C. where the proteinases self-digests.

Accordingly, the present method is directed to improving the standard molecular biology diagnostic technique, such as PCR, and minimising contamination of samples as a result of opening and shutting sample tubes.

The new procedures are directed to purify nucleic acid by requiring the tube only be opened to add the sample initially and then subsequently opening it for PCR.

The two proteinases described (EA1 and Ak1) are both destabilised by chelators and are intrinsically both less stable and therefore easier to remove at the end of the treatment compared to previously used thermophilic enzymes.

The present invention also prevents unwanted degradation of the nucleic acid sample by cellular enzymes upon cell lysis, as the lysis step is carded out at 75° C. where these enzymes are inactive. This is a significant improvement over current methods using Proteinase K at lower temperatures, where nucleic acid degradation cannot be avoided.

Both enzymes are carefully selected to be active at high temperature but can still be killed at the end of the procedure with the enzymatic activity being stopped with greater assurance. It is essential to inactivate these enzymes or they can potentially attack the enzyme carrying out the PCR reaction. Preferred proteinases are derived from *Bacillus* as previously mentioned being Ak1 and EA1.

This invention demonstrates the possibility for use of a range of thermophilic proteinases in nucleic acid-based applications, particularly for faster and simplified methods for the preparation of DNA samples Aspects of the present invention have been described by way of example only and it should be appreciated that modifications and additions may be made thereto without departing from the scope thereof as defined in the appended claims.

What we claimed is:

1. A method for amplifying deoxyribonucleic acid (DNA) for testing, comprising:

i) adding *Bacillus* EA1 thermophilic proteinase to a sample comprising deoxyribonucleic nucleic acid (DNA) for testing, thereby forming a system, wherein the thermophilic proteinase digests protein in the sample and is capable of auto-catalysis at or above 90° C.;

ii) closing the system;

iii) incubating said sample in said system for a period at 65-80° C. as required to effect one or more of: lysis of one or more cells, digestion of one or more proteins, or digestion of one or more cell-wall enzymes, via activity of said thermophilic proteinase;

iv) incubating the sample in said system at or above 90° C. to effect auto-catalysis of the thermophilic proteinase;

v) opening the system;

vi) providing polymerase chain reaction (PCR) reagents to the sample; and vii) amplifying the DNA for testing by PCR, wherein the protein and thermophilic proteinase are denatured in the system prior to opening without the addition of further denaturing agents.

2. The method as claimed in claim 1, wherein the sample is incubated for a total of 45 minutes or less.

3. The method as claimed in claim 1, wherein the incubation temperature required to effect one or more of the lysis of cells, digestion of proteins, or digestion of cell-wall enzymes is 75° C.

4. The method as claimed in claim 1, wherein the sample is incubated at 94° C. to effect auto-catalysis of the thermophilie proteinase.

5. The method as claimed in claim 1, including an initial step of adding at least one mesophilic enzyme with the *Bacillus* EA1 thermophilic proteinase to the sample, and wherein prior to incubation at 65-80° C. the sample is incubated for a period below 40° C. as required to effect removal of any cell walls via activity of said at least one mesophilic enzyme.

6. The method as claimed in claim 5, wherein said at least one mesophilic enzyme is a cellulase.

7. The method as claimed in claim 5, wherein the initial incubation temperature required to effect removal of any cell walls is 37° C.

* * * * *